United States Patent [19]
Keck

[11] Patent Number: 5,874,160
[45] Date of Patent: Feb. 23, 1999

[54] MACROFIBER NONWOVEN BUNDLE

[75] Inventor: Laura Elizabeth Keck, Alpharetta, Ga.

[73] Assignee: Kimberly-Clark Worldwide, Inc., Neenah, Wis.

[21] Appl. No.: 771,622

[22] Filed: Dec. 20, 1996

[51] Int. Cl.$^6$ .............................. B32B 27/14; A47K 7/02
[52] U.S. Cl. .................. 428/198; 428/219; 428/311.51; 428/401; 442/350; 442/351; 442/362; 442/364; 15/208; 15/228
[58] Field of Search .................................... 428/198, 219, 428/311.51, 401, 373, 374; 442/350, 351, 362, 364; 15/208, 228

[56] References Cited

U.S. PATENT DOCUMENTS

| | | | |
|---|---|---|---|
| 3,146,479 | 9/1964 | Stoker | 15/118 |
| 3,338,992 | 8/1967 | Kinney | 264/24 |
| 3,341,394 | 9/1967 | Kinney | 161/72 |
| 3,345,668 | 10/1967 | Forrest | 15/209 |
| 3,423,266 | 1/1969 | Davies et al. | 156/167 |
| 3,502,763 | 3/1970 | Hartmann | 264/210 |
| 3,537,121 | 11/1970 | McAvoy | 15/230.12 |
| 3,542,615 | 11/1970 | Dobo et al. | 156/181 |
| 3,608,708 | 9/1971 | Storandt | 206/46 R |
| 3,689,617 | 9/1972 | Fairbanks | 264/103 |
| 3,692,618 | 9/1972 | Dorschner et al. | 161/72 |
| 3,802,817 | 4/1974 | Matsuki et al. | 425/66 |
| 3,849,241 | 11/1974 | Butin et al. | 161/169 |
| 3,855,046 | 12/1974 | Hansen et al. | 161/150 |
| 3,910,284 | 10/1975 | Orentreich | 128/355 |
| 3,965,519 | 6/1976 | Hermann | 15/104.93 |
| 4,041,203 | 8/1977 | Brock et al. | 428/157 |
| 4,055,029 | 10/1977 | Kalbow | 51/395 |
| 4,298,649 | 11/1981 | Meitner | 428/198 |
| 4,307,143 | 12/1981 | Meitner | 252/91 |
| 4,322,308 | 3/1982 | Hooper et al. | 252/107 |
| 4,340,563 | 7/1982 | Appel et al. | 264/518 |
| 4,374,888 | 2/1983 | Bornslaeger | 428/198 |
| 4,462,135 | 7/1984 | Sanford | 15/105 |
| 4,462,981 | 7/1984 | Smith | 424/27 |
| 4,525,411 | 6/1985 | Schmidt | 428/198 |
| 4,533,399 | 8/1985 | Mencke | 134/6 |
| 4,567,011 | 1/1986 | Nalle, Jr. | 264/504 |
| 4,622,258 | 11/1986 | Mencke | 428/171 |
| 4,636,429 | 1/1987 | Morell et al. | 428/288 |
| 4,657,691 | 4/1987 | Hara et al. | 252/91 |
| 4,659,609 | 4/1987 | Lamers et al. | 428/194 |
| 4,663,220 | 5/1987 | Wisneski et al. | 428/221 |

(List continued on next page.)

FOREIGN PATENT DOCUMENTS

| | | | |
|---|---|---|---|
| 0067016 A1 | 5/1982 | European Pat. Off. | C11D 17/04 |
| 0084963 A2 | 1/1983 | European Pat. Off. | D04H 1/44 |
| 0287286 A2 | 4/1988 | European Pat. Off. | B24D 11/00 |
| 0032793 A2 | 9/1991 | European Pat. Off. | A47K 10/16 |
| 2513251 | 9/1976 | Germany | D01F 8/08 |
| 1258621 | 1/1969 | United Kingdom | B24B 29/00 |
| 2017485 | 2/1979 | United Kingdom | A47L 17/08 |
| 2142225 | 6/1984 | United Kingdom | A47L 13/16 |
| 95/00116 | 6/1994 | WIPO | A61K 7/50 |

OTHER PUBLICATIONS

*Polymer Blends and Composites* by John A. Manson and Leslie H. Sperling, Plenum Press, New York, 1976, pp. 273–277.

*Encyclopedia of Chemical Technology*, Fourth Ed., vol. 7, Composite Materials to Detergency, "Corrosion and Corrosion Control," pp. 572–619 and Detergency, pp. 1072–1117, John Wiley & Sons, New York.

*Primary Examiner*—Terrel Morris
*Attorney, Agent, or Firm*—Douglas H. Tulley, Jr.

[57] ABSTRACT

The present invention relates to a cleaning implement formed from spunbond fiber webs having a basis weight less than about 85 grams per square meter and wherein the fibers comprise macrofibers having an average fiber diameter greater than 50 microns and less than about 500 microns. A section of macrofiber web having a mass between about 10 and 30 grams is bundled into a deformable three-dimensional shape which is about 8 to 25 cm in at least one dimension. The cleaning implement is particularly well suited for use in conjunction with shower gels or soaps for washing the body.

30 Claims, 7 Drawing Sheets

U.S. PATENT DOCUMENTS

| | | | |
|---|---|---|---|
| 4,741,941 | 5/1988 | Englebert et al. | 428/71 |
| 4,755,247 | 7/1988 | Mudge | 156/244.15 |
| 4,769,022 | 9/1988 | Chang et al. | 604/368 |
| 4,775,582 | 10/1988 | Abba et al. | 428/288 |
| 4,793,941 | 12/1988 | Serbiak et al. | 252/91 |
| 4,795,668 | 1/1989 | Krueger et al. | 428/174 |
| 4,833,003 | 5/1989 | Win et al. | 428/198 |
| 4,879,084 | 11/1989 | Parnigoni | 264/295 |
| 4,954,281 | 9/1990 | Resch | 252/107 |
| 4,969,225 | 11/1990 | Schubert | 15/209 |
| 4,975,218 | 12/1990 | Rosser | 252/117 |
| 4,981,749 | 1/1991 | Kubo et al. | 442/364 |
| 5,030,292 | 7/1991 | Koike et al. | 134/32 |
| 5,053,157 | 10/1991 | Lloyd | 252/91 |
| 5,057,361 | 10/1991 | Sayovitz et al. | 428/290 |
| 5,057,368 | 10/1991 | Largman et al. | 428/397 |
| 5,064,556 | 11/1991 | Brandes et al. | 252/135 |
| 5,069,970 | 12/1991 | Largman et al. | 428/373 |
| 5,108,820 | 4/1992 | Kaneko et al. | 428/198 |
| 5,108,827 | 4/1992 | Gessner | 428/219 |
| 5,144,744 | 9/1992 | Campagnoli | 29/446 |
| 5,145,727 | 9/1992 | Potts et al. | 428/198 |
| 5,169,706 | 12/1992 | Collier, IV et al. | 428/152 |
| 5,178,931 | 1/1993 | Perkins et al. | 428/198 |
| 5,188,885 | 2/1993 | Timmons et al. | 428/198 |
| 5,277,976 | 1/1994 | Hogle et al. | 428/397 |
| 5,282,900 | 2/1994 | McDonell et al. | 134/2 |
| 5,294,482 | 3/1994 | Gessner | 428/287 |
| 5,296,158 | 3/1994 | MacGilp et al. | 252/108 |
| 5,324,618 | 6/1994 | Kawabe et al. | 430/191 |
| 5,336,552 | 8/1994 | Strack et al. | 428/224 |
| 5,382,400 | 1/1995 | Pike et al. | 264/168 |
| 5,412,830 | 5/1995 | Girardot et al. | 15/118 |
| 5,465,452 | 11/1995 | Girardot et al. | 15/210.1 |
| 5,466,410 | 11/1995 | Hills | 264/172.11 |
| 5,491,864 | 2/1996 | Tuthill et al. | 15/118 |
| 5,516,510 | 5/1996 | Beilfuss et al. | 424/65 |
| 5,534,339 | 7/1996 | Stokes | 442/362 |
| 5,597,645 | 1/1997 | Pike et al. | 442/362 |
| 5,605,749 | 2/1997 | Pike et al. | 442/60 |
| 5,652,051 | 7/1997 | Shawver et al. | 442/362 |

MACROFIBER NONWOVEN BUNDLE

FIELD OF THE INVENTION

The present invention relates to cleaning materials. More particularly, the present invention relates to a bundle of macrofiber nonwoven materials adapted for cleaning and washing surfaces in conjunction with cleaning agents.

BACKGROUND OF THE INVENTION

Woven, mesh and nonwoven materials have been used in various forms to carry and/or work surface active agents. Nonwoven materials have heretofore been used within wipes and cleaning pads. In addition, woven and mesh materials have been designed to apply liquid cleaning agents such as, for example, for use in cleaning and washing the body, especially for removing dirt and dead skin therefrom.

For example, U.S. Pat. Nos. 4,793,941 to Serviak et al. and 5,053,157 to Lloyd disclose a laundry detergent impregnated within a nonwoven web which is suitable for delivering a proper amount of detergent for each wash load. Similarly, U.S. Pat. No. 4,775,582 to Abba et al. discloses a meltblown nonwoven wet wipe for personal care uses. Although the prior art active agent impregnated nonwoven pads of microfibers may be useful in certain applications they may not be well suited to those applications requiring high strength or the ability to generate a rich lather in a scrubbing or cleaning action.

An improved and highly useful nonwoven pad for applying active agents is disclosed in U.S. Pat. No. 5,605,749, to Pike et al. which discloses a pad comprising a porous high loft structure of crimped conjugate spunbond fibers impregnated with a topically applicable active agent. A variety of active agents suitable for use with the pad include, for example, polishing agents, waxes, cleansers, moisturizers, germicidal solutions and/or topical medicaments. The pad disclosed in Pike et al. exhibits high strength and abrasion resistance while also having excellent absorbency. Thus, this pad exhibits both increased strength and an increased capacity to hold active agents relative to microfiber materials. Accordingly, the nonwoven pad of Pike et al. is an excellent structure for carrying and applying active agents in a variety of applications. However, in those applications in which it is desirable to generate a rich lather in the scrubbing action, a varied structure may be desirable. In addition, the increased absorbent characteristics of this pad may likewise be undesirable in certain applications, such as in a bath sponge where the excellent absorbency may cause the pad to become waterlogged or otherwise heavier than desired.

Hand held scrubbers comprising diamond mesh netting are disclosed in U.S. Pat. No. 4,462,135 to Sanford, U.S. Pat. No. 5,144,744 to Campagnoli and European Application publication No. WO 95/00116. These scrubbers employ a mesh netting and, thus, employ a uniform pattern of spaced intersecting strands. Such diamond mesh netting has long been used to wrap foodstuffs, fruit, poultry and other items for some time. However, the above referenced patents and application describe use of such mesh netting for use as a hand held scrubber.

However, many existing scrubbers suffer from a propensity to develop mold, mildew or growth of other organic matter. In this regard many soaps and shower gels support mold growth and, thus, designs which do not allow the scrubber to be efficiently rinsed of cleanser or allow the scrubber to dry quickly may accelerate the growth of mold or other organisms which is obviously undesirable. In addition, many scrubbers, such as many mesh netting scrubbers, fail to provide a soft and/or cloth-like feel whereas scrubbers with good hand and a softer feel are highly desirable in cleaning implements intended for washing the body, particularly when used to wash the more sensitive areas of the skin.

Therefore there exists a need for high strength nonwoven material having good abrasion resistance with a structure suitable for providing excellent lather generation and cleaning action. Moreover, there exists a need for a nonwoven material adapted for generating lather which dries quickly and which may be readily flushed of cleanser. Further, there exists a need for such a nonwoven material and scrubber made therefrom which provides improved tactile properties. Further, there exists a need for a nonwoven material and scrubber made therefrom which does not absorb excess cleanser and/or water when in use.

SUMMARY OF THE INVENTION

The aforesaid needs are fulfilled and problems experienced by those skilled in the art overcome by a cleaning implement of the present invention which comprises a bundle of one or more nonwoven webs having a basis weight of up to about 85 gsm and wherein the web comprises macrofibers having an average fiber diameter greater than 50 microns. In addition, the bundle can have a mass of from about 10 g to about 30 g, although desirably about 20 g. In a further aspect the bundle may have a length or diameter of from about 2 inches to about 10 inches, desirably from about 3 inches to about 6 inches. In a still a further aspect, the nonwoven macrofiber web within the bundle may have a plurality of pleats therein. Further, the cleaning implement may have a pliable and/or deformable three-dimensional shape; for example the bundle of nonwoven web may be substantially fan shaped or ball-like. In a further aspect the fibers may comprise macrofiber spunbond fibers having an average thickness or diameter between about 60 microns and 500 microns, more desirably having an average thickness or diameter between about 75 and 200 microns. In addition, the macrofibers may comprise monocomponent or multicomponent fibers such as, for example, bicomponent spunbond fibers having a sheath/core configuration wherein the sheath component comprises a polymer of ethylene and the core component comprises a polymer of propylene. In a further aspect, the fibers may be either crimped or uncrimped, although uncrimped fibers are generally preferred. In a further aspect the bundle is fixedly bound in a three-dimensional configuration having a length of at least 3 inches. In addition the bundle may comprise a plurality of sheets fixedly bound together wherein the majority of the surface area of each sheet is able to move freely with respect to the other sheets.

DEFINITIONS

Figure 1:
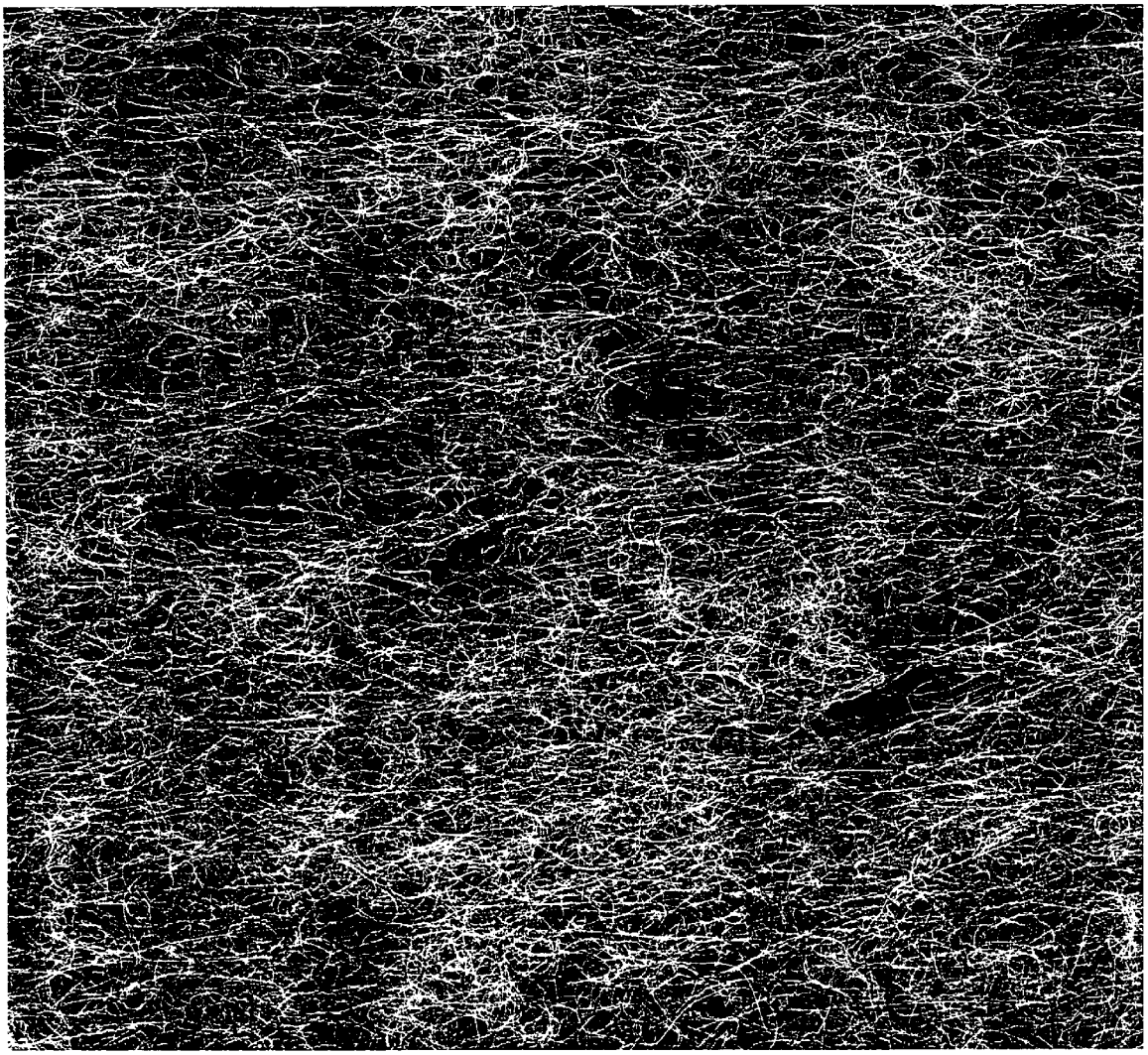
FIG. 1 is a photograph of a macrofiber web suitable for use with the present invention.

As used herein the term "nonwoven fabric" or "nonwoven web" means a web having a structure of individual fibers or threads which are randomly interlaid, but not in an identifiable manner as in a woven, knitted or mesh fabric. The basis weight of nonwoven fabrics is often expressed in ounces of material per square yard (osy) or grams per square meter (gsm) and the fiber diameters useful are usually expressed in microns.

As used herein the term "macrofibers" means fibers having an average thickness or diameter greater than 50 microns. For example, fibers having an average diameter of from about 60 microns to about 500 microns, or more particularly, macrofibers may have an average diameter of from about 75 microns to about 200 microns. In addition, macrofibers is intended to include agglomerated fibers comprised of a plurality of smaller diameter fibers which collectively have a thickness greater than 50 microns such as, for example, those shown in FIG. 4.

As used herein the term "spunbond fibers" refers to continuous fibers which are formed by extruding molten thermoplastic material as filaments from a plurality of fine, usually circular capillaries of a spinneret with the diameter of the extruded filaments then being reduced as by, for example, in U.S. Pat. No. 4,340,563 to Appel et al., and U.S. Pat. No. 3,692,618 to Dorschner et al., U.S. Pat. No. 3,802,817 to Matsuki et al., U.S. Pat. Nos. 3,338,992 and 3,341,394 to Kinney, U.S. Pat. No. 3,502,763 to Hartman, U.S. Pat. No. 3,542,615 to Dobo et al., U.S. Pat. No. 5,366,552 and U.S. Pat. No. 5,382,400 to Pike et al. Spunbond fibers are generally quenched and not tacky when they are deposited onto a collecting surface.

As used herein the term "meltblown fibers" means fibers formed by extruding a molten thermoplastic material through a plurality of fine, usually circular, die capillaries as molten threads or filaments into converging high velocity, usually hot, gas (e.g. air) streams which attenuate the filaments of molten thermoplastic material to reduce their diameter, which may be to microfiber diameter. Thereafter, the meltblown fibers are carried by the high velocity gas stream and are deposited on a collecting surface to form a web of randomly disbursed meltblown fibers. Such a process is disclosed, for example, in U.S. Pat. No. 3,849,241 to Buntin et al. Meltblown fibers are microfibers which may be continuous or discontinuous, are generally smaller than 10 microns in average diameter, and are generally tacky when deposited onto a collecting surface.

As used herein "multilayer laminate" means a laminate wherein some of the layers are spunbond and some meltblown such as a spunbond/meltblown/spunbond (SMS) laminate and others as disclosed in U.S. Pat. No. 4,041,203 to Brock et al., U.S. Pat. No. 5,169,706 to Collier, et al, U.S. Pat. No. 5,145,727 to Potts et al., U.S. Pat. No. 5,178,931 to Perkins et al. and U.S. Pat. No. 5,188,885 to Timmons et al. Such a laminate may be made by sequentially depositing onto a moving forming belt first a spunbond fabric layer, then a meltblown fabric layer and last another spunbond layer and then bonding the laminate in a manner described below. Alternatively, the fabric layers may be made individually, collected in rolls, and combined in a separate bonding step. Such fabrics usually have a basis weight of from about 0.1 to 12 osy (3.4 to 400 gsm), or more particularly from about 0.75 to about 3 osy. Multilayer laminates may also have various numbers of meltblown layers or multiple spunbond layers in many different configurations and may include other materials like films (F) or coform materials, e.g. SMMS, SM, SFS, etc. The macrofiber spunbond web may be laminated to other materials or layers of materials as desired.

As used herein the term "polymer" generally includes but is not limited to, homopolymers, copolymers, such as for example, block, graft, random and alternating copolymers, terpolymers, etc. and blends and modifications thereof. Furthermore, unless otherwise specifically limited, the term "polymer" shall include all possible geometrical configurations of the molecule. These configurations include, but are not limited to isotactic, syndiotactic and random symmetries.

As used herein the term "monocomponent" fiber refers to a fiber formed from one or more extruders using only one polymer. This is not meant to exclude fibers formed from one polymer to which small amounts of additives have been added for color, antistatic properties, lubrication, hydrophilicity, etc. These additives, e.g. titanium dioxide for color, are generally present in an amount less than 5 weight percent and more typically about 2 weight percent.

As used herein the term "multicomponent" refers to fibers which have been formed from at least two polymers extruded from separate extruders but spun together to form one fiber. Multicomponent fibers are also sometimes referred to as conjugate or bicomponent fibers. The polymers are usually different from each other though conjugate fibers may be monocomponent fibers in the sense that the respective components can comprise similar or identical polymers. The polymers are arranged in substantially constantly positioned distinct zones across the cross-section of the conjugate fibers and extend continuously along the length of the conjugate fibers. The configuration of such a conjugate fiber may be, for example, a sheath/core arrangement wherein one polymer is surrounded by another or may be a side by side arrangement, a pie arrangement or other arrangement. Conjugate fibers are taught in U.S. Pat. No. 5,108,820 to Kaneko et al., U.S. Pat. No. 4,795,668 to Krueger et al. and U.S. Pat. No. 5,336,552 to Strack et al. Conjugate fibers are also taught in U.S. Pat. No. 5,382,400 to Pike et al. and may be used to produce crimp in the fibers by using the differential rates of expansion and contraction of the two (or more) polymers. Crimped fibers may also be produced by mechanical means and by the process of German Patent DT 25 13 251 A1. The fibers may also have shapes such as those described in U.S. Pat. Nos. 5,277,976 to Hogle et al., U.S. Pat. No. 5,466,410 to Hills and 5,069,970 and 5,057,368 to Largman et al., which describe fibers with varied and unconventional shapes.

As used herein the term "biconstituent fibers" refers to fibers which have been formed from at least two polymers extruded from the same extruder as a blend. The term "blend" is defined below. Biconstituent fibers do not have the various polymer components arranged in relatively constantly positioned distinct zones across the cross-sectional area of the fiber and the various polymers are usually not continuous along the entire length of the fiber, instead usually forming fibrils or protofibrils which start and end at random. Biconstituent fibers are sometimes also referred to as multiconstituent fibers. Fibers of this general type are discussed in, for example, U.S. Pat. Nos. 5,108,827 and 5,294,482 to Gessner. Bicomponent and biconstituent fibers are also discussed in the textbook *Polymer Blends and Composites* by John A. Manson and Leslie H. Sperling, copyright 1976 by Plenum Press, a division of Plenum Publishing Corporation of New York, IBSN 0-306-30831-2, at pages 273 through 277.

As used herein the term "blend" means a mixture of two or more polymers while the term "alloy" means a sub-class of blends wherein the components are immiscible but have been compatibilized. "Miscibility" and "immiscibility" are defined as blends having negative and positive values, respectively, for the free energy of mixing. Further, "compatibilization" is defined as the process of modifying the interfacial properties of an immiscible polymer blend in order to make an alloy.

As used herein, the term "hot air knife" or HAK means a process of pre- or preliminarily bonding a thermoplastic fiber, particularly spunbond, web in order to give it sufficient integrity, i.e. increase the stiffness of the web, for further processing, but does not mean the relatively strong bonding of secondary bonding processes like through-air bonding, thermal bonding and ultrasonic bonding. A hot air knife is a device which focuses a stream of heated air at a very high flow rate, generally from about 1000 to about 10000 feet per minute (fpm) (305 to 3050 meters per minute), or more particularly from about 3000 to 5000 feet per minute (915 to 1525 m/min.) directed at the nonwoven web immediately after its formation. The air temperature is usually in the range of the melting point of at least one of the polymers used in the web, generally between about 200° and 550° F. (93° and 290° C.) for the thermoplastic polymers commonly used in spunbonding. The control of air temperature, velocity, pressure, volume and other factors helps avoid damage to the web while increasing its integrity. The HAK's focused stream of air is arranged and directed by at least one slot of about ⅛ to 1 inches (3 to 25 mm) in width, particularly about ⅜ inch (9.4 mm), serving as the exit for the heated air towards the web, with the slot running in a substantially cross-machine direction over substantially the entire width of the web. In other embodiments, there may be a plurality of slots arranged next to each other or separated by a slight gap. The slots are usually, though not essentially, continuous, and may be comprised of, for example, closely spaced holes. The HAK has a plenum to distribute and contain the heated air prior to its exiting the slot. The plenum pressure of the HAK is usually between about 1.0 and 12.0 inches of water (2 to 22 mm Hg), and the HAK is positioned between about 0.25 and 10 inches and more preferably 0.75 to 3.0 inches (19 to 76 mm) above the forming wire. In a particular embodiment the HAK plenum's cross sectional area for cross-directional flow (i.e. the plenum cross sectional area in the machine direction) is at least twice the total slot exit area. Since the foraminous wire onto which spunbond polymer is formed generally moves at a high rate of speed, the time of exposure of any particular part of the web to the air discharged from the hot air knife is less a tenth of a second and generally about a hundredth of a second in contrast with the through air bonding process which has a much larger dwell time. The HAK process has a great range of variability and controllability of many factors such as air temperature, velocity, pressure, volume, slot or hole arrangement and size, and the distance from the HAK plenum to the web. The HAK is further described in U.S. patent application Ser. No. 08/362,328 to Arnold et al., filed Dec. 22, 1994 and commonly assigned, the entire contents of which are incorporated herein by reference.

As used herein, through-air bonding or "TAB" means a process of bonding a nonwoven bicomponent fiber web in which air which is sufficiently hot to melt one of the polymers of which the fibers of the web are made is forced through the web. The air velocity is between 100 and 500 feet per minute and the dwell time may be as long as 6 seconds. The melting and resolidification of the polymer provides the bonding. Through-air bonding requires the melting of at least one component to accomplish bonding; it is particularly useful in bonding webs with two components like conjugate fibers or those which include an adhesive. In the through-air bonder, air having a temperature above the melting temperature of one component and below the melting temperature of another component is directed from a surrounding hood, through the web, and into a perforated roller supporting the web. Alternatively, the through-air bonder may be a flat arrangement wherein the air is directed vertically downward onto the web. The operating conditions of the two configurations are similar, the primary difference being the geometry of the web during bonding. The hot air melts the lower melting polymer component and thereby forms bonds between the filaments to integrate the web.

As used herein, "ultrasonic bonding" means a process performed, for example, by passing the fabric between a sonic horn and anvil roll as illustrated in U.S. Pat. No. 4,374,888 to Bornslaeger.

As used herein "thermal point bonding" involves passing a fabric or web of fibers to be bonded between a heated calender roll and an anvil roll. The calender roll is usually, though not always, patterned in some way so that the entire fabric is not bonded across its entire surface, and the anvil roll is usually flat. As a result, various patterns for calender rolls have been developed for functional as well as aesthetic reasons. One example of a pattern has points and is the Hansen Pennings or "H&P" pattern with about a 30% bond area with about 200 bonds/square inch as taught in U.S. Pat. No. 3,855,046 to Hansen and Pennings. The H&P pattern has square point or pin bonding areas wherein each pin has a side dimension of 0.038 inches (0.965 mm), a spacing of 0.070 inches (1.778 mm) between pins, and a depth of bonding of 0.023 inches (0.584 mm). The resulting pattern has a bonded area of about 29.5% when new. Another typical point bonding pattern is the expanded Hansen Pennings or "EHP" bond pattern which produces about a 15% bond area when new with a square pin having a side dimension of 0.037 inches (0.94 mm), a pin spacing of 0.097 inches (2.464 mm) and a depth of 0.039 inches (0.991 mm). Another typical point bonding pattern designated "714" has square pin bonding areas wherein each pin has a side dimension of 0.023 inches, a spacing of 0.062 inches (1.575 mm) between pins, and a depth of bonding of 0.033 inches (0.838 mm). The resulting pattern has a bonded area of about 15% when new. Yet another common pattern is the C-Star pattern which has a bond area of about 16.9% when new. The C-Star pattern has a cross-directional bar or "corduroy" design interrupted by shooting stars. Other common patterns include a diamond pattern with repeating and slightly offset diamonds with about a 16% bond area when new. Typically, the percent bonding area varies from around 10% to around 30% of the area of the fabric laminate web. As in well known in the art, the spot bonding holds the laminate layers together as well as imparts integrity to each individual layer by bonding filaments and/or fibers within each layer.

DETAILED DESCRIPTION OF THE INVENTION

The fabric of the present invention is particularly useful in the formation of washing and cleaning implements, particularly those for generating a lather, such as for example, those used in connection with washing and cleaning the body. In reference to the exemplary material shown in FIG. 1, the macrofiber web has a highly porous structure of heterogeneous sized and shaped voids. However, although having low coverage and numerous large voids, for example those about 3 mm in length or greater, the fabric retains both high strength and abrasion resistance.

Figure 2A:
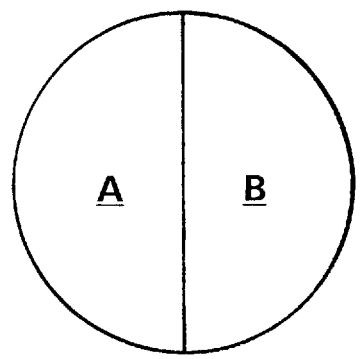
FIG. 2A is a schematic drawing illustrating the cross-section of a filament with the polymer components A and B in a side-by-side arrangement.
Figure 2B:
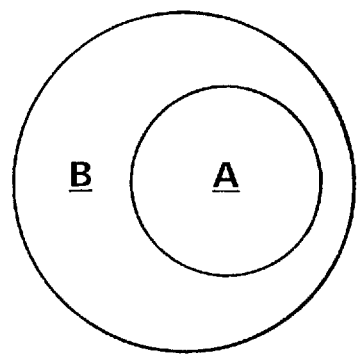
FIG. 2B is a schematic drawing illustrating the cross-section of a filament with the polymer components A and B in an eccentric sheath/core arrangement.
Figure 2C:
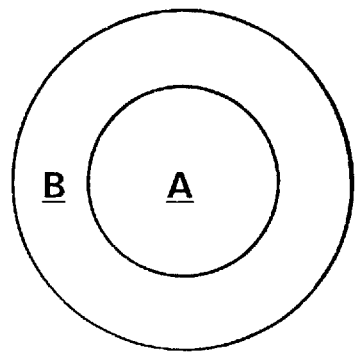
FIG. 2C is a schematic drawing illustrating the cross-section of a filament with the polymer components A and B in a concentric sheath/core arrangement.

The fabric of the present invention can comprise continuous melt-spun fibers, desirably spunbond fibers. The cleaning implement of the present invention comprises a web of macrofibers having an average fiber thickness or diameter greater than 50 $\mu$, desirably having an average fiber diameter between about 75 $\mu$ to about 200 $\mu$. Further, the macrofiber spunbond web should have a basis weight of from less than about 2.5 osy (85 gsm), desirably from about 2 osy (68 gsm) to about 0.5 osy (17 gsm). Although fibers having a substantially circular cross-section may be preferred with regard to the ease of fabrication, the macrofibers may have any one of numerous shapes such as, for example, multilobal or irregularly shaped fibers. Varied fiber shapes may be employed to provide a fabric with more texture or to increase the surface area of the fibers. In addition, the fibers may comprise either monocomponent or multicomponent fibers. In this regard, multicomponent fiber have preferred and desirably comprise a bicomponent fiber having a side-by-side configuration as shown in FIG. 2A, an eccentric sheath/core configuration as shown in FIG. 2B or a concentric sheath/core configuration as shown in FIG. 2C. However, other multicomponent fiber configurations as well as the use of more than two components may also be used in connection with the present invention. In addition, the fibers may comprise crimped and/or uncrimped continuous fibers, although uncrimped fibers are generally preferred. When employing crimped fibers, they desirably have a low crimp, such as less than about 2 per inch.

A wide variety of polymers are suitable for use with the present invention including, but not limited to, polyolefins (such as polymers of propylene and/or ethylene), polyesters, polyamides, polyurethanes and other melt-spinnable polymers. Exemplary polyolefins include one or more of polypropylene, polyethylene, ethylene copolymers, propylene copolymers, and butene copolymers. Useful polypropylenes include, for example, polypropylene available from the Exxon Chemical Company under the trade designation ESCORENE® PD3445, and linear low density polyethylene available from Dow Chemical Co. of Midland, Mich. under the trade designation ASPUN® 6811A and 2553. Numerous other polymers and formulations thereof suitable for melt-spinning are well known in the art. For example, particularly commercially useful polyamides are nylon-6, nylon 66, nylon-11 and nylon-12. These polyamides are commercially available from a number of sources such as Emser Industries of Sumter, S.C. (Grilon® & Grilamid® nylons) and Atochem Inc. Polymers Division, of Glen Rock, N.J. (Rilsan® nylons), among others.

In addition, suitable polymers include blends and biconstituent compositions. One particularly useful blend, for example, may include about 5 to about 20% by weight of an elastomeric thermoplastic material such as an ABA' block copolymer of styrene, ethylene and butylene. In one aspect, A and A' are each a thermoplastic polymer endblock which contains a styrenic moiety such as a poly (vinyl arene) and B is an elastomeric polymer midblock such as a conjugated diene or a lower alkene polymer. The fibers may be formed in part from, for example, an elastomer of (polystyrene/poly (ethylene-butylene)/polystyrene) block copolymers available from the Shell Chemical Co. under the trademark KRATON. Such copolymers are available in various formulations, some of which are described in U.S. Pat. No. 4,663,220.

Further, when using multicomponent spunbond fibers one skilled in the art will appreciate that polymer component A and polymer component B are desirably selected so that the resulting bicomponent filament may be readily bonded without affecting the structural integrity of the web. In this regard it is generally preferred that one of the polymer components A and B has a melting temperature greater than that of the other polymeric component. In one such embodiment, for example, polymer A comprises a propylene polymer and whereas polymer B comprises an ethylene polymer Suitable bicomponent fibers have from about 10% to about 90% by volume of one polymer component, desirably from about 20% to about 80%, more desirably from about 40% to 60% by volume of the fiber cross-section. Use of such configurations can also provide fibers which have a latent helical crimp, see U.S. Pat. No 5,382,400 to Pike et al. the entire contents of which are incorporated herein by reference. However, crimp may be imparted to the fibers by other means known in the art The polymers may further include additives, as is known in the art, to obtain increased strength, abrasion resistance, mold or mildew resistance, softness, and other desirable characteristics. Further, various dyes and/or pigments may be added to the polymer formulations to achieve a desired color and a more aesthetically pleasing product. Further, as is known in the art, the fabric may be treated with various surface treatments to impart other characteristics as desired such as, for example, imparting wettability with modified siloxanes as described in U.S. Pat. No. 5,057,361. However, in regard to wettability it should be noted that typically such treatment will be unnecessary as the surfactants and other materials found in the majority of cleansers inherently allow excellent wetting of the macrofiber spunbond material.

Figure 3:
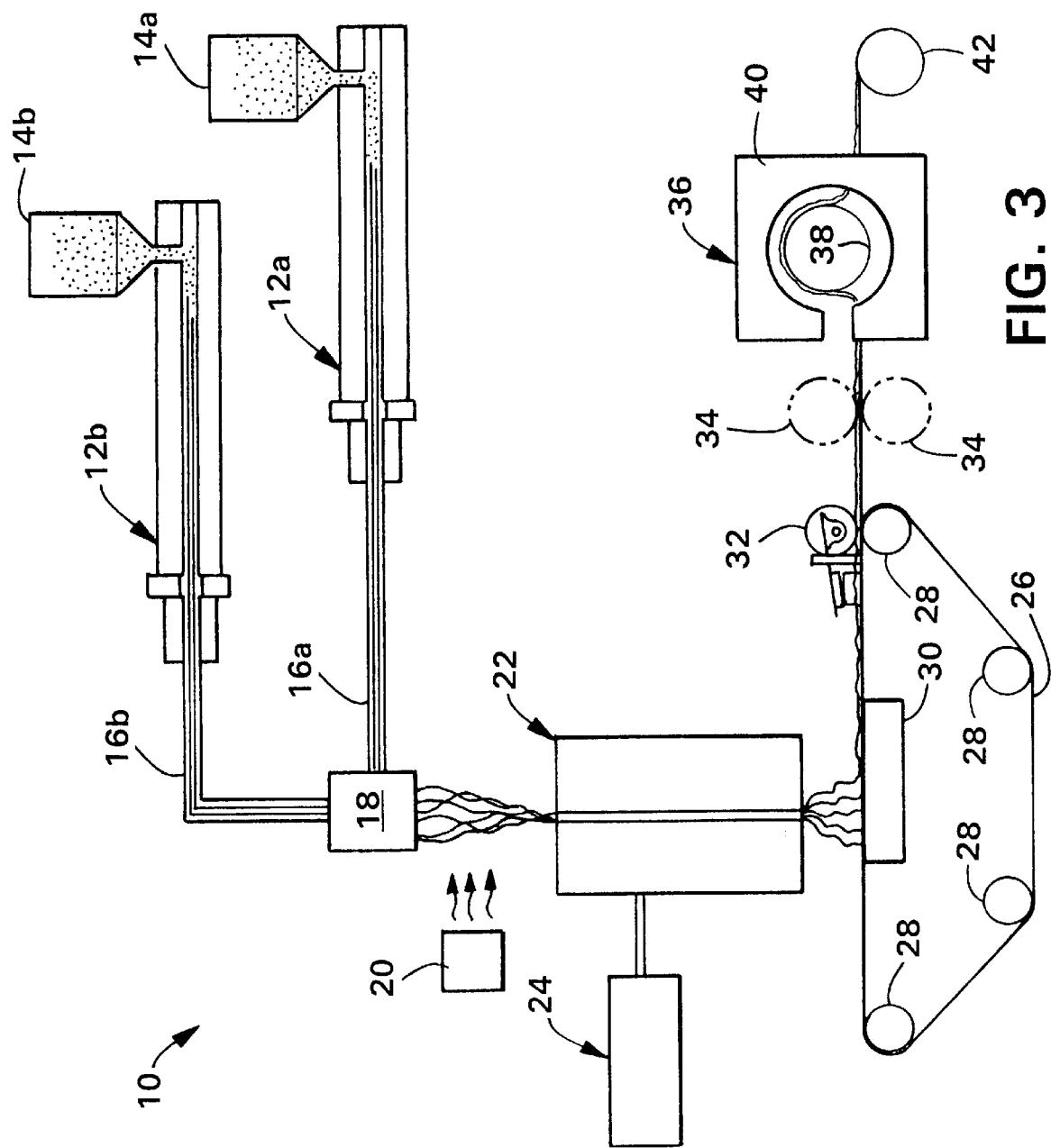
FIG. 3 is a schematic drawing of a process line for making a macrofiber spunbond web of the present invention.

Turning to FIG. 3, a process line 10 for preparing a preferred embodiment of the present invention is disclosed. The particular process line 10 depicted in FIG. 3 is arranged to produce bicomponent continuous filaments, but it should be understood that the present invention comprehends nonwoven fabrics made with monocomponent fibers as well as multicomponent fibers having more than two components. The process line 10 includes a pair of extruders 12a and 12b for separately extruding a polymer component A and a polymer component B. Polymer component A is fed into the respective extruder 12a from a first hopper 14a and polymer component B is fed into the respective extruder 12b from a second hopper 14b. Polymer components A and B are melted and extruded by the respective extruders 12a and 12b through polymer conduits 16a and 16b and the spinneret 18. Although the temperatures of the molten polymers vary depending on the polymers used, when polypropylene and polyethylene are used as components A and B respectively, the preferred temperatures of the polymers range from about 360° to about 530° F. and preferably range from 370° to about 430° F.

Spinnerets for extruding bicomponent filaments are well known to those of ordinary skill in the art and, generally described, include a housing containing a spin pack which includes a plurality of plates stacked one on top of the other with a pattern of openings arranged to create flow paths for directing polymer components A and B separately through the spinneret. The spinneret 18 has openings, spinholes, arranged in one or more rows. When the polymers are extruded through the spinholes they form a downwardly extending curtain of filaments.

As indicated hereinabove, the fabric of the present invention desirably has a combination of large fiber thicknesses while having low coverage. The fiber thickness and low coverage described herein may be achieved by employing a high throughput and line speed. Further, large diameter spinholes may likewise be employed to increase fiber thickness. Spinholes greater than 1 mm, for example about 1.5 mm, may be used in connection with the present process. The combination of the spinhole diameter, melt temperature, fiber draw unit manifold pressure and temperature can be varied in order to achieve the desired average fiber thickness.

The process line 10 also includes a quench blower 20 positioned adjacent the curtain of filaments extending from the spinneret 18. Air from the quench air blower 20 quenches the filaments extending from the spinneret 18. The quench air can be directed from one side of the filament curtain as shown in FIG. 1, or both sides of the filament curtain. As the extruded filaments extend below the spinneret 18, a stream of air from the quench blower 20 at least partially quenches the filaments. The quench air preferably flows in a direction substantially perpendicular to the length of the filaments at a temperature of about 45° to about 90° F. and a velocity from about 100 to about 400 feet per minute. After quenching, the filaments are drawn into the vertical passage of the fiber draw unit 22 by a flow of air from the air source 24 through the fiber draw unit. The fiber draw unit is preferably positioned 30 to about 60 inches below the bottom of the spinneret 18.

A fiber draw unit or aspirator 22 is positioned below the spinneret 18 and receives the quenched filaments. Fiber draw unit or aspirators for use in melt spinning polymers are well-known as discussed above. Suitable fiber draw units for use in the process of the present invention include a linear fiber aspirator of the type shown in U.S. Pat. No. 3,802 817 and eductive guns of the type shown in U.S. Pat. Nos. 3,692,618 and 3,423,266, the disclosures of which are incorporated herein by reference. Generally, described, the fiber draw unit 2 includes an elongate vertical passage through which the filaments are drawn by aspirating air entering from the sides of the passage and flowing downwardly through the passage. An air source 24 supplies air to the fiber draw unit 22. The air draws the filaments and ambient air through the fiber draw unit.

Figure 4:
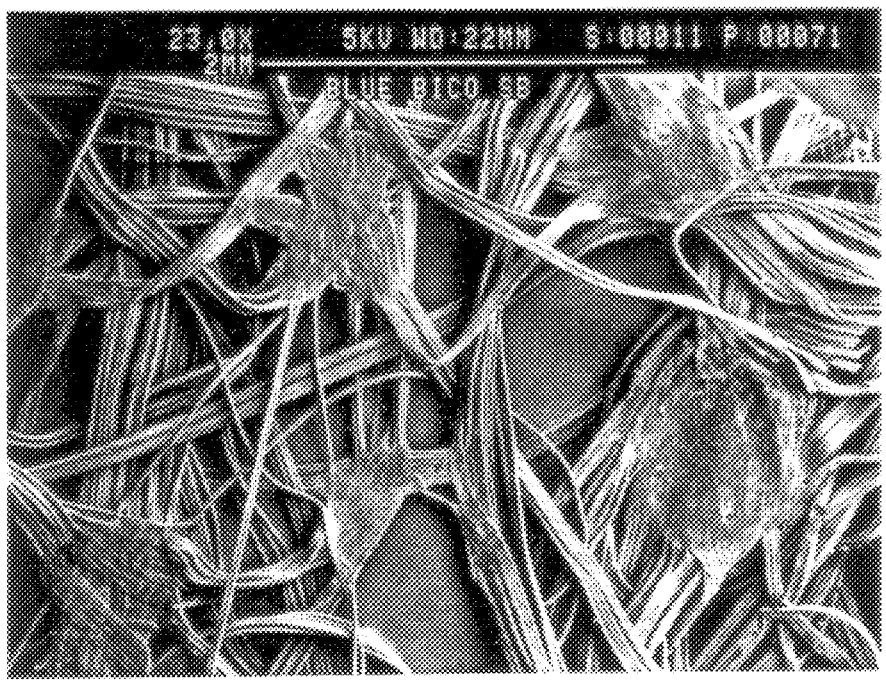
FIG. 4 is a photomicrograph of a point bonded macrofiber web suitable for use with the present invention.

An endless foraminous forming surface 26 is positioned below the fiber draw unit 22 and receives the continuous filaments from the outlet opening of the fiber draw unit. The forming surface 26 travels around guide rollers 28. A vacuum 20 positioned below the forming surface 26 where the filaments are deposited draws the filaments against the forming surface to form an unbonded, nonwoven web of continuous filaments. The web can then be lightly compressed by the compression roller 32 and then thermal point bonded by rollers 34 (shown in phantom) or through-air bonded in the through-air bonder 36. In the through-air bonder 36, air having a temperature above the melting temperature of component B and below the melting temperature of component A is directed from the hood 40, through the web, and into the perforated roller 38. The hot air melts the lower melting polymer component B and thereby forms bonds between the bicomponent filaments to integrate the web. When polypropylene and polyethylene are used as polymer components A and B respectively, the air flowing through the through-air bonder preferably has a temperature ranging from about 230° to about 280° F. and a velocity from about 100 to about 500 feet per minute. The dwell time of the web in the through-air bonder is preferably less than about 5 seconds. It should be understood, however, that the parameters of the through-air bonder depend on factors such as the type of polymers used and thickness of the web. Alternatively or in addition to HAK or TAB bonding, the process line may include other in-line bonding apparatus such as, for example, thermal point bonding roller 34 (shown in phantom). A through-air bonded macrofiber bicomponent spunbond web is shown in FIG. 1 and a thermal point bonded macrofiber spunbond web is shown in FIG. 4. Although the methods of bonding of the webs shown in FIGS. 1 and 4 are through-air bonded and thermal point bonded respectively, it should be understood that the fabric of the present invention may be bonded by other means such as oven bonding, ultrasonic bonding, adhesive bonding, or combinations thereof. Such bonding techniques are well-known to those of ordinary skill in the art and are not discussed here in detail.

The macrofiber web can then be wound onto the winding roller 42 and is ready for further processing as desired. In this regard the macrofiber web may then be bundled or bunched into a cleaning implement as desired. A desired cleaning implement of the present invention can have diameter of from about 2 to about 10 inches, desirably from about 3 to 6 inches in diameter. Additionally, a desired cleaning implement of the present invention comprises about 10 g to about 30 g of material, more desirably about 20 g of material. Although this will vary with the particular basis weight of the macrofiber web, such a cleaning implement may often comprise about 1 square yard of fabric.

Figure 5:
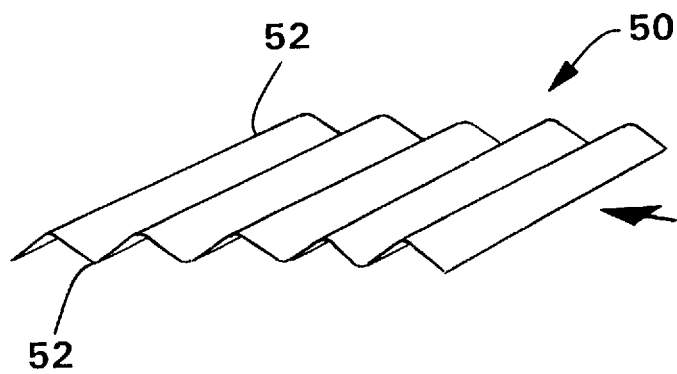
FIG. 5 is a drawing of a pleated macrofiber spunbond web of the present invention suitable for making the bundle of FIG. 6.
Figure 6:
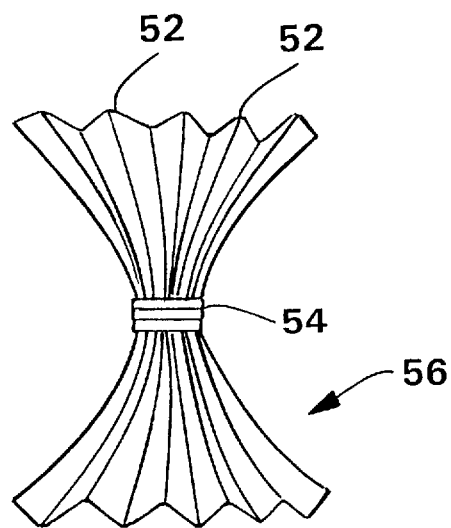
FIG. 6 is a drawing of an exemplary macrofiber spunbond bundle of the present invention.

The macrofiber web may be bundled or bunched into a fan-like, ball-like or other three-dimensional shape by hand and held in position by a tie or elastic band. In a preferred embodiment, the cleaning implement 56 may comprise a pleated fan shaped article as shown in FIG. 6. A swatch of material 50, for example about 1 square yard, may be cut from the roll and then folded accordion style in about 1 inch increments or less, such as shown in FIG. 5, to create a series of pleats 52. The pleated material may then be bound or permanently cinched, such as by a band 54, substantially along its central axis resulting in a fan shaped cleaning implement of FIG. 6. However, it will be appreciated that the macrofiber web may be formed into various other three-dimensional configurations which are likewise suitable for use as a cleaning implement, desirably such configurations are bound in a manner which provides for a pliable and deformable implement. It should be further noted that a highly desirable aspect of such designs is that the material is folded or bent onto itself yet is not a compact tightly bound structure which allows for space between the respective layers or pleats as well as movement of the same across one another. The swatch may also be folded along a central axis onto itself one or more times or loosely rolled prior to being bound in order to produce a more layered bundle. In addition, multiple sections or sheets may be bound together forming a single three-dimensionally shaped cleaning implement; the independent sections may be separately or collectively pleated and/or folded prior to being bound together.

A great number and variety of cleaning agents are known in the art and also widely commercially available. A listing of many such detergents are compiled in *McCutcheon's Emulsifiers and Detergents—North American Edition* 1996, vol. 1. (MC Publishing). Cleaning agents suitable for use with the present invention preferably include lathering cleansers such as, for example, those commonly intended for washing or cleaning the body. Desired cleaning agents used in connection with the present invention include soaps (i.e. natural soaps and synthetic detergents) and may come in various forms such as, for example, liquid, gels or semi-solid creams. Of course, many solid form cleansers, such as common bar soap, may also be suitable for use with the present invention since when used in conjunction with the excess water in bathing or showering, an emulsion is generated with the gentle scrubbing or cleaning action. Numerous formulations of natural soaps and synthetic detergents are known in the art. Generally mild soaps and/or synthetic detergents are preferred such as, for example, sodium or potassium lauroyl sarcosinate, alkyly glyceryl ether sulfonate, sulfonated fatty esters and sulfonated fatty acids, desirably ethoxylated alkyl sulfates and mixtures thereof are preferred such as, for example, $C_{12}$–$C_{14}$ alkyl anionic surfactants selected from the group of sodium alkyl glycerol ether sulfonate or sodium alkyl sulfate. Mild detergents are also described in U.S. Pat. No. 5,296,158 to MacGilp et al., U.S. Pat. No. 4,975,218 to Rosser and U.S. Pat. No. 5,324,618 to Kamegai et al. Numerous liquid soaps, creams and gels are also commercially available for use as a cleanser for the body such as, for example, Softsoap®, Sani-Fresh® Premium, Eurobath® etc. Anti-microbial soaps and/or detergents are also known in the art such as, for example, those described in U.S. Pat. No. 4,954,281 and commercially available soaps including Lever 2000® antibacterial liquid soap (Lever Brothers), and Dial® antibacterial liquid soap (Dial Corporation). Further, it is known that the soap or detergent formulation may include deodorizing agents or fragrances such as, for example, those described in U.S. Pat. No. 5,516,510 to Beifuss et al. and U.S. Pat. No. 4,322,308 to Hooper et al. Moreover, it is known in the art to combine additional optional ingredients within the soap or detergent formulation as desired including, but not limited to, moisturizers/skin conditioners, preservatives, thickeners or viscosity modifiers, dyes, sequestering agents, pH adjusters, etc. Examples of many of such materials are described in R. Kirk and D. Othmer, *Encyclopedia of Chemical Technology*, $4^{th}$ ed. Vol. 7, ppg. 572–619 and 1072–1117. The particular formulation of the cleansing agent is not believed limited by the present invention although those formulations whether are highly producing a rich lather are highly desired.

The cleansing agent is desirably applied to the macrofiber spunbond bundle just before or contemporaneously with the scrubbing or cleansing action. The cleansing agent may be applied, such as by hand, directly to the bundle or first to the surface to be cleaned, i.e. the skin, so that the cleansing agent is transferred to the bundle with the scrubbing or cleaning action.

Example 1

Figure 7:
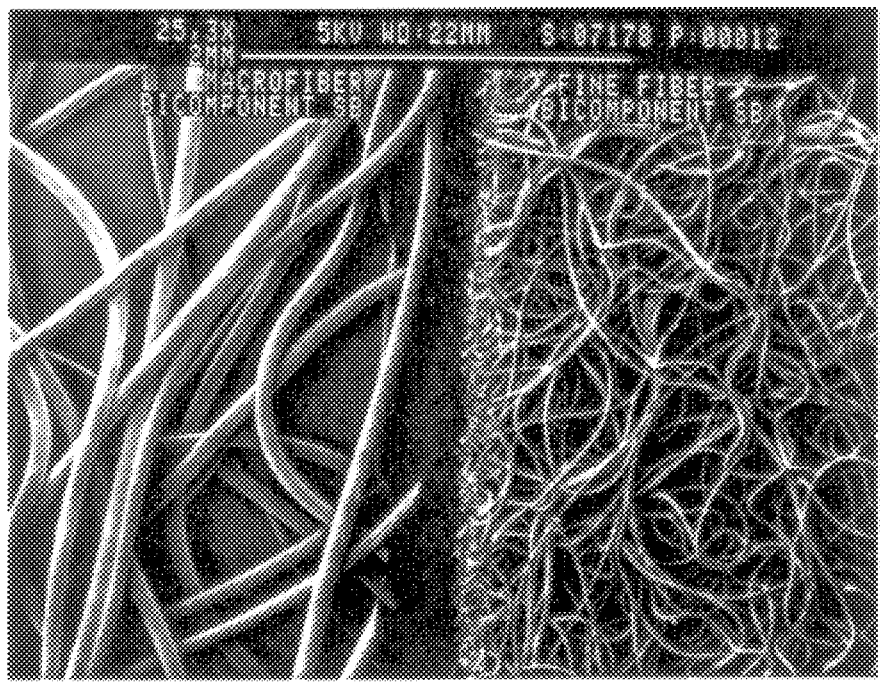
FIG. 7 is a photomicrograph showing the macrofiber spunbond web of Example 1 and the high loft crimped spunbond web of comparative Example 4.
Figure 8:
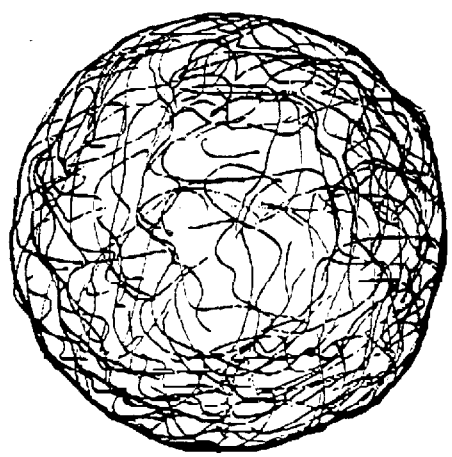
FIG. 8 is a drawing of a bundled nonwoven cleaning implement of the present invention in a ball-like configuration.

A 1.0 osy (34 gsm) spunbond bicomponent fiber was produced using the production process disclosed hereinabove. A polyethylene polymer, ASPUN® 6811A which is commercially available from Dow, was fed into a first single screw extruder. A polypropylene polymer, PD 3445 which is commercially available from Exxon, was fed into a second single screw extruder. The extruded polymers were spun into substantially round bicomponent fibers having a side-by-side configuration with each component comprising about 50% by volume of the fiber using a bicomponent spin pack which had 12 holes/inch, a 1.4 mm spinhole diameter and a 2.6:1 L/D ratio. The extruder temperature was 380° F. (193° C.) and the pack temperature was 400° F. (204° C.) and the spinhole throughput was 3.0 ghm (grams per hole per minute). The bicomponent fibers exiting the spinholes were quenched by a flow of air having a flow rate of about 45 standard feet$^3$/minute/inch (0.5 m$^3$/minute/cm) at 59° F. (15° C.). The quenched fibers were drawn in an aspirator unit of the type which is described in U.S. Pat. No. 3,802,817 to Matsuki et al. The quenched fibers were drawn with air having a temperature of 56° F. (13° C.) and the manifold pressure at 1 psig. The forming height was approximately 8 inches (20.5 cm). The drawn fibers were then deposited onto a foraminous forming surface with the assist of a vacuum flow to form an unbonded fiber web. The line speed of the foraminous forming surface was 166 feet/minute (51 m/minute). The unbonded fiber web was then preliminarily bonded with a hot air knife at 350° F. (177° C.) and at a 0.5 inch (1.3 cm) height above the forming wire. The lightly bonded fiber web was then thermal point bonded with a spiral EHP pattern roller wherein the bonded surface area of the fabric was about 5%. The calendar rolls were heated at 275° F. (135° C.) and at 50 psi. The bonded fabric was then, off-line, further bonded by passing the web through a through-air bonder equipped with a heated air source. The air temperature was about 260° F. (127° C.) with a pressure drop of 1 inch (2.54 cm) of water and with damper position at 30% open area. The residence time in the hood was about 3 seconds. The resulting nonwoven web is shown in FIG. 1, having a basis weight of about 1.0 osy (34 gsm) and an average fiber diameter of about 75 microns. An enlarged photomicrograph of the web formed in accord with this example is also shown in FIG. 7 designated as "MACROFIBER BICOMPONENT SB".

Example 2

A 1.0 osy (34 gsm) spunbond bicomponent fiber was produced using the production process disclosed hereinabove. A random copolymer of propylene and ethylene (3% ethylene), available from Union Carbide under the designation 6D43, was fed into a first single screw extruder. A polypropylene polymer, PD 3445 which is commercially available from Exxon, was fed into a second single screw extruder. Blue pigment 11111 from Standridge Color Corporation was added to the sheath component (the random copolymer fed into the first extruder) comprising about 2% by weight of the polymer. The extruded polymers were spun into substantially round bicomponent fibers having a sheath/core configuration with each component comprising about 50% by volume using a bicomponent spin pack, which had 12 holes/inch, a 1.4 mm spinhole diameter and a 2.6:1 L/D ratio. The extruder temperature was 430° F. (221° C.) and the spinhole throughput was 1.5 ghm (grams per hole per minute). The bicomponent fibers exiting the spinholes were quenched by a flow of air having a flow rate of about 45 standard feet$^3$/minute/inch (0.5 m$^3$/minute/cm). The quenched fibers were drawn in an aspirator unit of the type which is described in U.S. Pat. No. 3,802,817 to Matsuki et al. The drawn fibers were then deposited onto a foraminous forming surface with the assist of a vacuum flow to form an unbonded fiber web. The unbonded fiber web was then bonded by passing the web through heated calender rolls at 280° F. (138° C.) having an EHP bond pattern providing about a 15% bonding area. The resulting nonwoven web is shown in FIG. 4, having a basis weight of about 1.0 osy (34 gsm). The average fiber diameter, of the fine individual fibers, was about 30 microns. However, lengthwise bonding or "roping" of two or more fine fibers created macrofibers with an average macrofiber thickness in excess of 60 microns.

Example 3

A 1.25 osy (42 gsm) spunbond bicomponent fiber was produced using the production process disclosed hereinabove. A polyethylene polymer, ASPUN® 6811A which is commercially available from Dow, was fed into a first single screw extruder. A polypropylene polymer, PD 3445 which is commercially available from Exxon, was fed into a second single screw extruder. The extruded polymers were spun into substantially round bicomponent fibers having a side-by-side configuration with each component comprising about 50% by volume of the fiber using a bicomponent spin pack which had 12 holes/inch, a 1.4 mm spinhole diameter and a 2.6:1 L/D ratio. The extruder temperature was 380° F. (193° C.) and the pack temperature was about 390° F. (199° C.) and the spinhole throughput was 4.5 ghm (grams per hole per minute). The bicomponent fibers exiting the spinholes were quenched by a flow of air having a flow rate of about 45 standard feet$^3$/minute/inch (0.5 m$^3$/minute/cm). The quenched fibers were drawn in an aspirator unit of the type which is described in U.S. Pat. No. 3,802,817 to Matsuki et al. The quenched fibers were drawn with air having a temperature of 66° F. (19° C.) and the manifold pressure at 1 psig. The forming height was approximately 8 inches (20.5 cm). The drawn fibers were then deposited onto a foraminous forming surface with the assist of a vacuum flow to form an unbonded fiber web. The line speed of the foraminous forming surface was 217 feet/minute (66 m/minute). The unbonded fiber web was then bonded by passing the web through a through-air bonder equipped with a heated air source. The air temperature was about 290° F. (143° C.), at a pressure drop of 1.6 inches (4.1 cm) of water, with damper position at 98% open area. The residence time in the hood was about 1 second. The resulting nonwoven web is shown in FIG. 1, having a basis weight of about 1.25 osy (42 gsm) and an average fiber diameter of about 100 microns.

(Comparative) Example 4

A nonwoven web of bicomponent spunbond material was made in accord with the process described in U.S. patent application Ser. No. 08/363,096, now U.S. Pat. No. 5,605, 749 (hereinafter Pike '749) to create a 3 osy (102 gsm) bicomponent spunbond fabric of crimped 50/50 side-by-side fibers of polyethylene and polypropylene. The resulting web had an average fiber thickness of 19 microns. A photomicrograph of this web is shown in FIG. 7 designated as "FINE FIBER BICOMPONENT SB."

As shown in FIG. 7, the absorbent high loft structure of Pike '749 provides a fabric with fine fibers, high loft and very good coverage. Contra, the combination of the large fiber thickness and the low basis weight provides a structure with low coverage, i.e. numerous large voids many of which extend through the entire z direction or bulk of the fabric. Although Pike '749 has a large void volume due to the fiber crimp and high loft structure, this is unlike the void spacing in the fabric of the present invention in terms of both size and continuity of the void structure.

While the invention has been particularly shown and described with reference to preferred embodiments thereof, it will be understood by those skilled in the art that other changes in form and details may be made therein without departing from the spirit and scope of the invention.

What is claimed is:

1. A cleaning implement comprising a gathered nonwoven sheet fixedly bound in a deformable three-dimensional configuration wherein said nonwoven sheet has a basis weight of less than about 85 gsm and comprises macrofibers having an average thickness greater than 50 microns and less than 500 microns.

2. A cleaning implement of claim 1 wherein said implement has a mass of from about 10 g to about 30 g.

3. A cleaning implement of claim 1 wherein said implement has a mass of about 20 g.

4. A cleaning implement of claim 2 wherein said implement is from about 2 inches to about 10 inches in at least one dimension.

5. A cleaning implement of claim 4 wherein said implement is from about 3 inches to about 6 inches in at least one dimension.

6. A cleaning implement of claim 5 wherein implement has a mass of about 20 g.

7. A cleaning implement of claim 2 wherein said macrofiber web has a plurality of pleats therein.

8. A cleaning implement of claim 7 wherein said macrofibers have an average fiber thickness of from about 75 microns to about 200 microns.

9. A cleaning instrument of claim 2 wherein said bundle is substantially fan shaped.

10. A cleaning implement of claim 5 wherein said fixedly bound gathered nonwoven sheet is ball shaped.

11. A cleaning implement of claim 1 wherein said macrofibers comprise multicomponent fibers.

12. A cleaning implement of claim 11 wherein said fibers comprise continuous bicomponent spunbond fibers having a sheath/core configuration.

13. A cleaning implement of claim 12 wherein said bicomponent fibers have a concentric sheath/core configuration.

14. A cleaning implement of claim 12 wherein said fibers are uncrimped fibers.

15. A cleaning implement of claim 13 wherein said sheath component comprises an ethylene polymer and said core component comprises a propylene polymer.

16. A cleaning implement of claim 11 wherein said bicomponent fibers have a side-by-side configuration.

17. A cleaning implement of claim 2 wherein said macrofibers have an average fiber diameter of from about 60 microns to about 200 microns.

18. A cleaning implement of claim 2 wherein said average fiber diameter is between 75 microns and 200 microns.

19. A cleaning implement of claim 1 wherein said bundle is fixedly bound in a deformable three-dimensional configuration having a length of at least 3 inches.

20. A cleaning implement of claim 2 wherein said bundle comprises a plurality of sections fixedly bound together wherein the majority of the surface area of each sheet is able to move against adjacent sheets.

21. A cleaning implement of claim 1 wherein said macrofibers comprise a plurality of smaller diameter fibers bonded along their lengths wherein said bonded fibers collectively have an average thickness greater than 50 microns.

22. A cleaning implement of claim 19 wherein said implement contains a cleaning agent.

23. A cleaning implement of claim 22 wherein said cleaning agent includes an anti-bacterial agent.

24. A cleaning implement of claim 22 wherein said cleaning agent includes an anti-fungal agent.

25. A cleaning implement of claim 24 wherein said cleaning agent includes a skin moisturizer.

26. A cleaning implement of claim 22 wherein said macrofibers comprise continuous spunbond fibers having an average fiber diameter between about 75 microns and 200 microns.

27. A cleaning implement of claim 22 wherein said macrofibers comprise a plurality of smaller diameter fibers bonded along their lengths wherein said bonded fibers collectively have an average thickness greater than 50 microns.

28. The cleaning implement of claim 2 wherein said macrofibers comprise a plurality of lengthwise bonded fibers.

29. The cleaning implement of claim 2 wherein said cleaning implement comprises a plurality of independent sections of nonwoven material.

30. The cleaning implement of claim 19 wherein said cleaning implement comprises a plurality of independent sections of nonwoven material.

* * * * *

UNITED STATES PATENT AND TRADEMARK OFFICE
CERTIFICATE OF CORRECTION

PATENT NO. : 5,874,160
DATED : February 23, 1999
INVENTOR(S) : Laura Elizabeth Keck It is certified that error appears in the above-identified patent and that said Letters Patent is hereby corrected as shown below:

Column 7, Line 34, "fiber have" should read -- fibers are --
Column 10, Line 31, "can have diameter" should read -- can have a diameter --
Column 11, Line 49, "whether are highly" should read -- which are capable of --

Signed and Sealed this

Tenth Day of October, 2000

Attest:

Attesting Officer

Q. TODD DICKINSON
Director of Patents and Trademarks